(12) United States Patent
Machida et al.

(10) Patent No.: US 10,351,538 B2
(45) Date of Patent: Jul. 16, 2019

(54) METHODS RESPECTIVELY FOR PRODUCING 2,4,6-TRIS (2-HYDROXY-3-METHYL-4-ALKOXYPHENYL)-1,3,5-TRIAZINE COMPOUND AND 2,4,6-TRIS(2,4-DIHYDROXY-3-METHYLPHENYL)-1,3,5-TRIAZINE

(71) Applicant: KANEKA CORPORATION, Osaka-shi (JP)

(72) Inventors: Koji Machida, Takasago (JP); Akira Nishiyama, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/758,807

(22) PCT Filed: Sep. 1, 2016

(86) PCT No.: PCT/JP2016/075705
§ 371 (c)(1),
(2) Date: Mar. 9, 2018

(87) PCT Pub. No.: WO2017/043416
PCT Pub. Date: Mar. 16, 2017

(65) Prior Publication Data
US 2018/0305325 A1 Oct. 25, 2018

(30) Foreign Application Priority Data

Sep. 9, 2015 (JP) ................................. 2015-177994

(51) Int. Cl.
*C07D 251/24* (2006.01)
*C07D 251/28* (2006.01)
*G02B 1/14* (2015.01)
*B32B 7/02* (2019.01)
*G02B 5/30* (2006.01)

(52) U.S. Cl.
CPC ............. *C07D 251/24* (2013.01); *B32B 7/02* (2013.01); *C07D 251/28* (2013.01); *G02B 5/30* (2013.01); *G02B 1/14* (2015.01)

(58) Field of Classification Search
CPC ............................ C07D 251/24; C07D 251/28
USPC ........................................ 544/216, 218, 219
See application file for complete search history.

(56) References Cited

U.S. PATENT DOCUMENTS

| | | | | |
|---|---|---|---|---|
| 6,184,375 | B1 * | 2/2001 | Huglin | A61K 8/4966 544/116 |
| 6,297,378 | B1 * | 10/2001 | Gupta | C07D 251/24 544/216 |
| 7,553,892 | B2 * | 6/2009 | Negishi | C08K 5/3492 523/122 |
| 2007/0215845 | A1 | 9/2007 | Negishi et al. | |
| 2009/0258976 | A1 | 10/2009 | Negishi et al. | |
| 2011/0087023 | A1 | 4/2011 | Kamimoto et al. | |

FOREIGN PATENT DOCUMENTS

| | | |
|---|---|---|
| JP | 2004-160883 A | 6/2004 |
| JP | 2009-292753 A | 12/2009 |
| JP | 2009-292754 A | 12/2009 |
| JP | 2016-139027 | 8/2016 |
| WO | 2005/109052 A1 | 11/2005 |
| WO | 2009/148040 A1 | 12/2009 |

OTHER PUBLICATIONS

JP 2004160883, Jun. 10, 2004; EPO English Translation.*
International Search Report dated Nov. 8, 2016, in PCT/JP2016/075705, filed Sep. 1, 2016.

* cited by examiner

*Primary Examiner* — Venkataraman Balasubramanian
(74) *Attorney, Agent, or Firm* — Oblon, McClelland, Maier & Neustadt, L.L.P.

(57) ABSTRACT

The present invention provides methods respectively for producing a 2,4,6-tris(2-hydroxy-3-methyl-4-alkoxyphenyl)-1,3,5-triazine compound and 2,4,6-tris(2,4-dihydroxy-3-methylphenyl)-1,3,5-triazine, both of which are improved in yield and quality. The methods according to the present invention are characterized in that a reaction of 2,4,6-tris(2,4-dihydroxy-3-methylphenyl)-1,3,5-triazine with an alkylating agent is carried out using a base in the presence of an alcohol or water, and are also characterized in that an ester compound is used as an additive in a reaction of cyanuric chloride with 2-methylresorcinol.

16 Claims, No Drawings

METHODS RESPECTIVELY FOR PRODUCING 2,4,6-TRIS (2-HYDROXY-3-METHYL-4-ALKOXYPHENYL)-1,3,5-TRIAZINE COMPOUND AND 2,4,6-TRIS(2,4-DIHYDROXY-3-METHYLPHENYL)-1,3,5-TRIAZINE

TECHNICAL FIELD

The present invention relates to methods for producing a 2,4,6-tris(2-hydroxy-3-methyl-4-alkoxyphenyl)-1,3,5-triazine compound useful as ultraviolet absorber and for producing 2,4,6-tris(2,4-dihydroxy-3-methylphenyl)-1,3,5-triazine as a raw material of the 2,4,6-tris(2-hydroxy-3-methyl-4-alkoxyphenyl)-1,3,5-triazine compound.

TECHNICAL BACKGROUND

Many functional films having optical properties are used as display-related materials. However, these materials are susceptible to degradation by ultraviolet light. Therefore, an ultraviolet absorber having excellent absorption capability with respect to various wavelength ranges is used for improving light fastness. Among ultraviolet absorbers, a 2,4,6-tris(2-hydroxy-3-methyl-4-alkoxyphenyl)-1,3,5-triazine compound is an ultraviolet absorber having an excellent ultraviolet absorbing ability in a long wavelength region, and thus, is expected for use in applications, such as a polarizer protective film, requiring absorption capability in a long wavelength region.

As a production method of the 2,4,6-tris(2-hydroxy-3-methyl-4-alkoxyphenyl)-1,3,5-triazine compound, a method is known in which a reaction of 2,4,6-tris(2,4-dihydroxy-3-methylphenyl)-1,3,5-triazine with an alkyl halide is carried out using dimethylformamide as a solvent and potassium carbonate as a base (Patent Document 1).

Further, as production methods of the 2,4,6-tris(2,4-dihydroxy-3-methylphenyl)-1,3,5-triazine, a method in which a reaction of cyanuric chloride with 2-methylresorcinol is carried out in presence of aluminum chloride using chlorobenzene as a solvent and cyclopentyl methyl ether as an additive (Patent Document 2), and a method in which sulfolane is used as a solvent (Patent Document 3), are known.

RELATED ART

Patent Documents

Patent Document 1: Japanese Patent Laid-Open Publication No. 2004-160883.
Patent Document 2: Japanese Patent Laid-Open Publication No. 2009-292754.
Patent Document 3: Japanese Patent Laid-Open Publication No. 2009-292753.

SUMMARY OF THE INVENTION

Problems to be Solved by the Invention

However, as examined by the present inventors, it is found that, in the production of 2,4,6-tris(2,4-dihydroxy-3-methylphenyl)-1,3,5-triazine, in the method described in the prior art in which cyclopentyl methyl ether is used, there is a problem that impurities represented by the following formula (4):

[Chemical Formula 1]

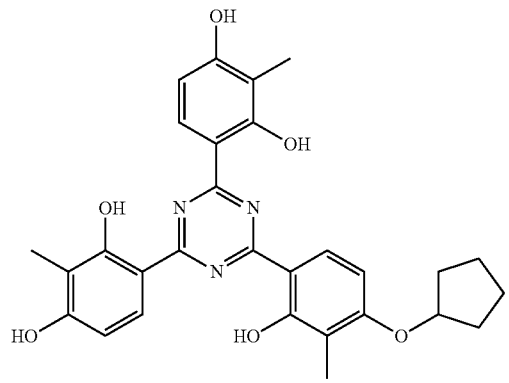

(4)

are by-produced, and yield and quality are greatly reduced.

Further, it is found that, in the production of the 2,4,6-tris(2-hydroxy-3-methyl-4-alkoxyphenyl)-1,3,5-triazine compound, in the method described in the prior art, there is a problem that impurities represented by the following formula (5):

[Chemical Formula 2]

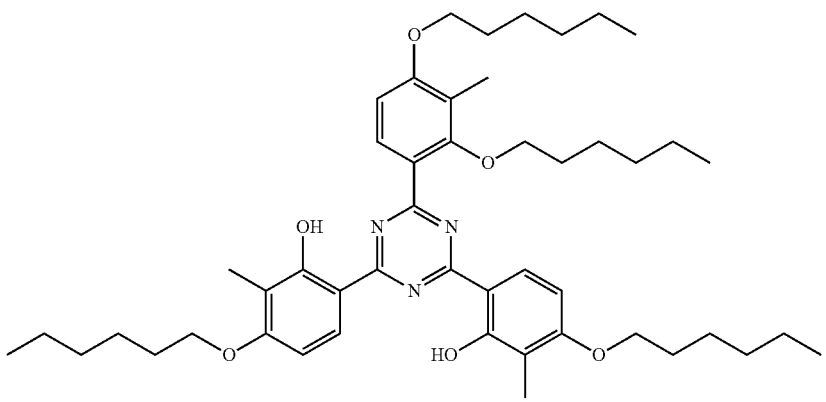

(5)

generated as a result that 2,4,6-tris(2-hydroxy-3-methyl-4-hexyloxyphenyl)-1,3,5-triazine, which is a target product, is further alkylated are by-produced, and, as is expected, yield and quality are greatly reduced.

A problem to be solved by the present invention with respect to the above-described technical background is to provide a production method that allows yield and quality to be improved in the production of the 2,4,6-tris(2-hydroxy-3-methyl-4-alkoxyphenyl)-1,3,5-triazine compound represented by the general formula (3) below. Further, another problem to be solved by the present invention is to provide a production method that allows yield and quality to be improved in the production of 2,4,6-tris(2,4-dihydroxy-3-methylphenyl)-1,3,5-triazine represented by a formula (1).

Means for Solving the Problems

As a result of intensive studies to solve the above-mentioned problems, the present inventors found that, by carrying out the reaction of 2,4,6-tris(2,4-dihydroxy-3-methylphenyl)-1,3,5-triazine with an alkylating agent using a base in presence of an alcohol or water, excessive alkylation is suppressed, and yield and quality of the 2,4,6-tris(2-hydroxy-3-methyl-4-alkoxyphenyl)-1,3,5-triazine compound, which is a target product, are improved. Further, the present inventors also found that, in the reaction of cyanuric chloride with 2-methylresorcinol, by using an ester compound as an additive, impurities are suppressed, and yield and quality of 2,4,6-tris(2,4-dihydroxy-3-methylphenyl)-1,3,5-triazine, which is a target product, are improved.

In the following, the present invention is described.

[1] A production method of a 2,4,6-tris(2-hydroxy-3-methyl-4-alkoxyphenyl)-1,3,5-triazine compound represented by the following general formula (3):

[Chemical Formula 4]

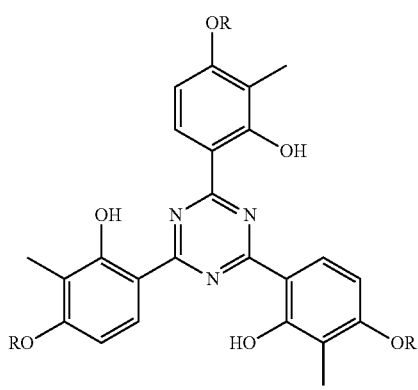
(3)

[where R represents a $C_{1-10}$ alkyl group], includes a process of causing 2,4,6-tris(2,4-dihydroxy-3-methylphenyl)-1,3,5-triazine represented by the following formula (1):

[Chemical Formula 3]

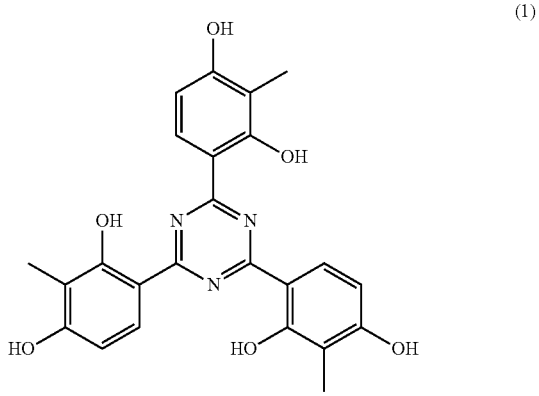 [SMILES: Cc1c(O)ccc(-c2nc(-c3ccc(O)c(C)c3O)nc(-c3ccc(O)c(C)c3O)n2)c1O]
(1)

to react with an alkylating agent represented by a general formula (2): RX [where R represents a $C_{1-10}$ alkyl group, and X represents a leaving group] in a solvent containing an alcohol or water in presence of a base.

[2] In the production method according to the above-described aspect [1], R is a hexyl group or a butyl group.

[3] In the production method according to the above-described aspect [1] or [2], X is a bromine atom, an iodine atom, or a methanesulfonyloxy group.

[4] In the production method according to any one of the above-described aspects [1]-[3], the alcohol is at least one selected from a group consisting of ethanol, 1-propanol, 2-propanol, 1-butanol and 1-hexanol.

[5] The production method according to any one of the above-described aspects [1]-[4] further includes a process of obtaining the compound (3) represented by the general formula (3) as a solid by neutralizing a reaction solution by adding an acid aqueous solution after the reaction.

[6] The production method according to any one of the above-described aspects [1]-[5] further includes a process of producing the compound (1) represented by the formula (1) by causing cyanuric chloride to react with 2-methylresorcinol in presence of a Lewis acid and an ester compound as an additive.

[7] In the production method according to the above-described aspect [6], the ester compound is at least one selected from a group consisting of ethyl acetate, isopropyl acetate, and hexyl acetate.

[8] A production method of 2,4,6-tris(2,4-dihydroxy-3-methylphenyl)-1,3,5-triazine represented by the following formula (1):

[Chemical Formula 5]

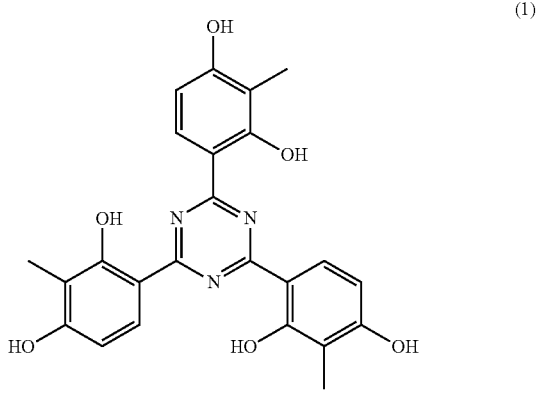
(1)

includes causing cyanuric chloride to react with 2-methylresorcinol in presence of a Lewis acid and an ester compound as an additive.

[9] In the production method according to the above-described aspect [8], the ester compound is at least one selected from a group consisting of ethyl acetate, isopropyl acetate, and hexyl acetate.

[10] A production method of a polarizer protective film includes: a process of producing the compound (3) using the method according to any one of the above-described aspects [1]-[7]; a process of obtaining a thermoplastic resin composition by at least mixing a thermoplastic resin and the compound (3); and a process of forming the thermoplastic resin composition into a film-like shape.

[11] A production method of a polarizing plate includes a process of laminating a polarizer protective film produced using the method according to the above-described aspect [10] on at least one side of a polarizer.

Effect of Invention

According to the present invention, yield and quality of the 2,4,6-tris(2-hydroxy-3-methyl-4-alkoxyphenyl)-1,3,5-triazine compound represented by the above formula (3) can be improved. Further, yield and quality of 2,4,6-tris(2,4-dihydroxy-3-methylphenyl)-1,3,5-triazine represented by the above formula (1) can be improved.

Mode for Carrying Out the Invention

In the following, embodiments of the production methods of the 2,4,6-tris(2-hydroxy-3-methyl-4-alkoxyphenyl)-1,3,5-triazine compound and 2,4,6-tris(2,4-dihydroxy-3-methylphenyl)-1,3,5-triazine are described. However, the present invention is not limited to these.

[Triarylation Process]

First, a production method of 2,4,6-tris(2,4-dihydroxy-3-methylphenyl)-1,3,5-triazine represented by the following reaction scheme is described.

[Chemical Formula 6]

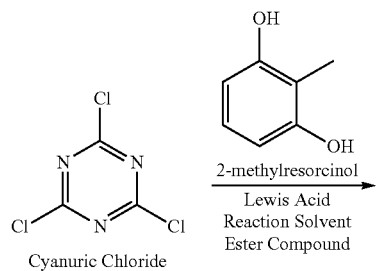

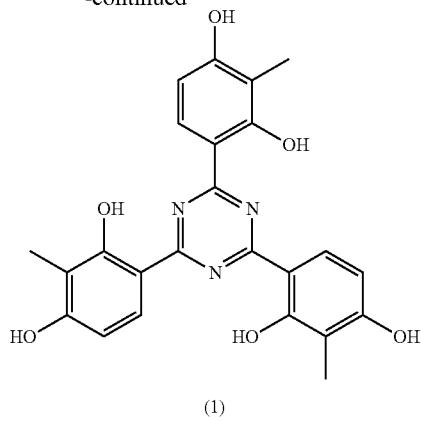

(1)

In the present invention, for example, a reaction is carried out by adding a reaction solvent and an ester compound as an additive to cyanuric chloride and, after adjusting temperature, adding Lewis acid and 2-methylresorcinol.

The reaction solvent is not particularly limited as long as the reaction solvent does not affect the reaction. Specifically, for example, ether-based solvents such as tetrahydrofuran, methyl tetrahydrofuran, diethyl ether, 1,4-dioxane, methyl tert-butyl ether, and ethylene glycol dimethyl ether; nitrile-based solvents such as acetonitrile, and propionitrile; aliphatic hydrocarbon-based solvents such as pentane, hexane, heptane, and methylcyclohexane; aromatic hydrocarbon-based solvents such as benzene, toluene, xylene, ethylbenzene, and mesitylene; ketone-based solvents such as acetone, methyl ethyl ketone, and methyl isobutyl ketone; halogen-based solvents such as methylene chloride, 1,2-dichloroethane, and chlorobenzene; sulfoxide-based solvents such as dimethyl sulfoxide, and sulfolane; amide-based solvents such as N,N-dimethylformamide, N,N-dimethylacetamide, N,N-diethylacetamide, N-methyl-2-pyrrolidone, N-ethyl-2-pyrrolidone, N-methyl-ε-caprolactam, and hexamethylphosphoramide; urea-based solvents such as dimethylpropylene urea; phosphonic acid triamide-based solvents such as hexamethylphosphonic acid triamide; and the like can be used. These solvents may each be independently used, or two or more of these solvents may be used in combination. When two or more of the solvents are used in combination, mixing ratios thereof are not particularly limited. Preferred solvents are halogen-based solvents such as methylene chloride, 1,2-dichloroethane, and chlorobenzene; sulfoxide-based solvent such as dimethyl sulfoxide, and sulfolane; amide-based solvents such as N,N-dimethylformamide, N,N-dimethylacetamide, N,N-diethylacetamide, N-methyl-2-pyrrolidone, N-ethyl-2-pyrrolidone, N-methyl-ε-caprolactam, and hexamethylphosphoramide; and urea-based solvents such as dimethylpropylene urea. More preferred solvents are chlorobenzene, sulfolane, N,N-dimethylformamide, and N,N-dimethylacetamide.

A too large amount of the solvent to be used is not preferable from a point of view of cost and a post-treatment. Therefore, an upper limit of the amount of the solvent to used with respect to 1 part by weight of the cyanuric chloride is preferably 100 times by weight, more preferably 50 times by weight, and particularly preferably 20 times by weight. A lower limit of the amount of the solvent to used with respect to 1 part by weight of the cyanuric chloride is preferably is preferably 0.1 times by weight, more preferably 0.5 times by weight, and particularly preferably 1 times by weight.

A particularly preferred solvent is chlorobenzene. An amount of chlorobenzene to be used is not particularly limited. However, the amount of chlorobenzene with respect to 1 part by weight of the cyanuric chloride is preferably 80 times by weight or less, more preferably 40 times by weight or less, and particularly preferably 20 times by weight or less. A lower limit of the amount of chlorobenzene is not particularly limited, but is preferably 2 times by weight or more, more preferably 5 times by weight or more, and particularly preferably 10 times by weight or more.

Although a definite action mechanism of the ester compound is unknown, it is presumed that a coordination ability of the ester compound with respect to the Lewis acid is involved. That is, when an additive having a high coordination ability is used, since the coordination ability with respect to the Lewis acid is too strong, progress of the reaction is inhibited. On the other hand, when an additive having a low coordination ability is used, there is a risk that the reaction may proceed too rapidly. As an additive of a reaction solvent for the synthesis of the 2,4,6-tris(2,4-dihydroxy-3-methylphenyl)-1,3,5-triazine compound according to the present invention, the ester compound is most suitable from a point of view of coordination ability. The ester compound has a moderate coordination ability and can moderately control a reactivity of the Lewis acid, and thus, yield and purity of the compound (1) are improved.

The ester compound as an additive is not particularly limited. However, examples of the ester compound include formate ester, acetic ester, propionate ester, butyric acid ester, isobutyric acid ester, benzoic acid ester, malonic esters, lactone, and the like. Further, the examples include $C_{1-6}$ alkyl ester, $C_{3-6}$ cycloalkyl ester, $C_{7-12}$ alkyl ester, $C_{6-12}$ aryl ester, $C_{6-12}$ aryl-$C_{1-6}$ alkyl ester, and the like. Specifically, the examples include methyl formate, ethyl formate, propyl formate, isopropyl formate, butyl formate, hexyl formate, methyl acetate, ethyl acetate, propyl acetate, isopropyl acetate, butyl acetate, isobutyl acetate, s-butyl acetate, t-butyl acetate, amyl acetate, isoamyl acetate, s-amyl acetate, t-amyl acetate, hexyl acetate, cyclohexyl acetate, octyl acetate, isooctyl acetate, nonyl acetate, decyl acetate, phenyl acetate, benzyl acetate, phenethyl acetate, methyl propionate, ethyl propionate, propyl propionate, isopropyl propionate, butyl propionate, hexyl propionate, methyl butyrate, ethyl butyrate, propyl butyrate, isopropyl butyrate, butyl butyrate, hexyl butyrate, methyl isobutyrate, ethyl isobutyrate, propyl isobutyrate, isopropyl isobutyrate, butyl isobutyrate, hexyl isobutyrate, methyl octanoate, methyl benzoate, ethyl benzoate, propyl benzoate, isopropyl benzoate, butyl benzoate, hexyl benzoate, dimethyl malonate, diethyl malonate, dimethyl succinate, diethyl succinate, γ-butyrolactone, δ-pentolactone, and the like. Ethyl acetate, propyl acetate, isopropyl acetate, butyl acetate, isobutyl acetate, s-butyl acetate, t-butyl acetate, amyl acetate, isoamyl acetate, s-amyl acetate, t-amyl acetate, and hexyl acetate are preferable. Ethyl acetate, isopropyl acetate, and hexyl acetate are more preferable.

An amount of the ester compound to be used is not particularly limited. However, the amount of the ester compound with respect to 1 part by weight of the cyanuric chloride is preferably 60 parts by weight or less, more preferably 30 parts by weight or less, and particularly preferably 15 parts by weight or less. A lower limit of the amount of the ester compound is not particularly limited, but is preferably 0.01 parts by weight or more, more preferably 0.1 parts by weight or more, and particularly preferably 1 part by weight or more.

The Lewis acid used in the present invention is not particularly limited as long as the Lewis acid promotes the reaction according to the present invention. However, examples of the Lewis acid include magnesium chloride, magnesium bromide, aluminum chloride, aluminum bromide, zinc chloride, tin (IV) chloride, iron (III) chloride, antimony fluoride (V), antimony chloride (V), phosphorus trichloride, phosphorus pentachloride, phosphorus oxychloride, titanium tetrachloride, titanium trichloride, zirconium chloride, hafnium chloride, tetraisopropoxytitanium, scandium trifluoromethanesulfonate (III), niobium trichloride, niobium pentachloride, boron trifluoride, boron trifluoride-diethyl ether complex, boron trichloride, boron tribromide, and the like. Among these Lewis acids, aluminum chloride is preferable.

An amount of the Lewis acid to be used is not particularly limited. However, the amount of the Lewis acid with respect to 1 mole of the cyanuric chloride is preferably 8 moles or less, more preferably 4 moles or less, and particularly preferably 2 moles or less. A lower limit of the amount of the Lewis acid is not particularly limited, but is preferably 0.2 moles or more, more preferably 0.5 moles or more, and particularly preferably 1 mole or more.

An amount of the 2-methylresorcinol to be used is not particularly limited. However, the amount of the 2-methylresorcinol with respect to 1 mole of the cyanuric chloride is preferably 16 moles or less, more preferably 8 moles or less, and particularly preferably 4 moles or less. A lower limit of the amount of the 2-methylresorcinol is not particularly limited, but is preferably 0.7 moles or more, more preferably 1.5 moles or more, and particularly preferably 3 moles or more.

A form of adding Lewis acid and 2-methyl resorcinol is not particularly limited. However, Lewis acid and 2-methyl resorcinol may be added in a form of solids or in a state of being dissolved or suspended in a solvent.

After the cyanuric chloride, the reaction solvent and the ester compound are mixed, temperature may be temporarily adjusted. The temperature may be appropriately set, but can be, for example, 20° C. or more and 80° C. or less.

A reaction temperature of the present process is not particularly limited, but is preferably not higher than a boiling point of the reaction solvent, more preferably 80° C. or lower, and particularly preferably 50° C. or lower. A lower limit of the reaction temperature is not particularly limited, but is preferably not lower than a melting point of the reaction solvent, more preferably 0° C. or higher, and particularly preferably 30° C. or higher.

An order of addition of the reagents in the present process is not particularly limited. However, the Lewis acid may be added to a solution to which the cyanuric chloride, the reaction solvent and the ester compound are added, and subsequently the 2-methylresorcinol may be added. Or, the 2-methyl resorcinol may be added to a solution to which the cyanuric chloride, the reaction solvent and the ester compound are added, and subsequently the Lewis acid may be added. Further, it is also possible that the Lewis acid and the 2-methylresorcinol are added at the same time.

After completion of the reaction, it is preferable to perform a general post-treatment. For example, excess Lewis acid is hydrolyzed by adding an inert solvent such as toluene and raising the temperature and further adding a hydrochloric acid. Next, after distilling off water content by heating distillation, a solid precipitated by cooling is filtered off, and the obtained solid is washed sequentially with toluene or the like and water or the like, and thereby, a crude product of the compound (1) is obtained. When necessary, it is also possible that the crude product is reslurried with water or the like and then filtered, and thereby, remaining aluminum and an acidic component are removed to increase purity.

An amount of the inert solvent such as toluene to be used in the treatment after the reaction is not particularly limited. However, the amount of the inert solvent with respect to 1 part by weight of the cyanuric chloride is preferably 60 parts by weight or less, more preferably 30 parts by weight or less, and particularly preferably 15 parts by weight or less. A lower limit of the amount of the inert solvent is not particularly limited, but is preferably 1 part by weight or more, more preferably 2 parts by weight or more, and particularly preferably 5 parts by weight or more.

A concentration of the hydrochloric acid used for the treatment after the reaction is not particularly limited. However, the concentration of the hydrochloric acid with respect to the entire reaction solution is preferably 35 wt % or less, more preferably 30 wt % or less, and particularly preferably 20 wt % or less. A lower limit of the concentration of the hydrochloric acid is not particularly limited, but is preferably 5 wt % or more, more preferably 10 wt % or more, and particularly preferably 15 wt % or more.

An amount of the hydrochloric acid to be used is not particularly limited. However, the amount of the hydrochloric acid with respect to 1 mole of the cyanuric chloride is, for example, 16 moles or less, preferably 8 moles or less, and more preferably 4 moles or less. A lower limit of the amount of the hydrochloric acid is not particularly limited, but is, for example, 0.7 moles or more, preferably 1.5 moles or more, and more preferably 3 moles or more.

A temperature at which the hydrochloric acid is added is not particularly limited, but is preferably not higher than a boiling point of the reaction solvent, more preferably 150° C. or lower, and particularly preferably 100° C. or lower. A lower limit of the temperature at which the hydrochloric acid is added is not particularly limited, but is preferably not lower than a melting point of the reaction solvent, more preferably 30° C. or higher, and particularly preferably 50° C. or higher.

The temperature at which the solid is precipitated by cooling is not particularly limited, but is preferably 70° C. or lower, more preferably 50° C. or lower, and particularly preferably 30° C. or lower. A lower limit of the temperature at which the solid is precipitated is not particularly limited, but is preferably not lower than a melting point of the reaction solvent, more preferably −40° C. or higher, and particularly preferably −20° C. or higher.

A method for separating the solid is not particularly limited, but a solid of a target substance can be obtained using a method such as vacuum filtration, pressure filtration, or centrifugation.

[Trialkylation Process]

Next, a production method of the 2,4,6-tris(2-hydroxy-3-methyl-4-alkoxyphenyl)-1,3,5-triazine compound represented by the following reaction scheme is described.

[Chemical Formula 7]

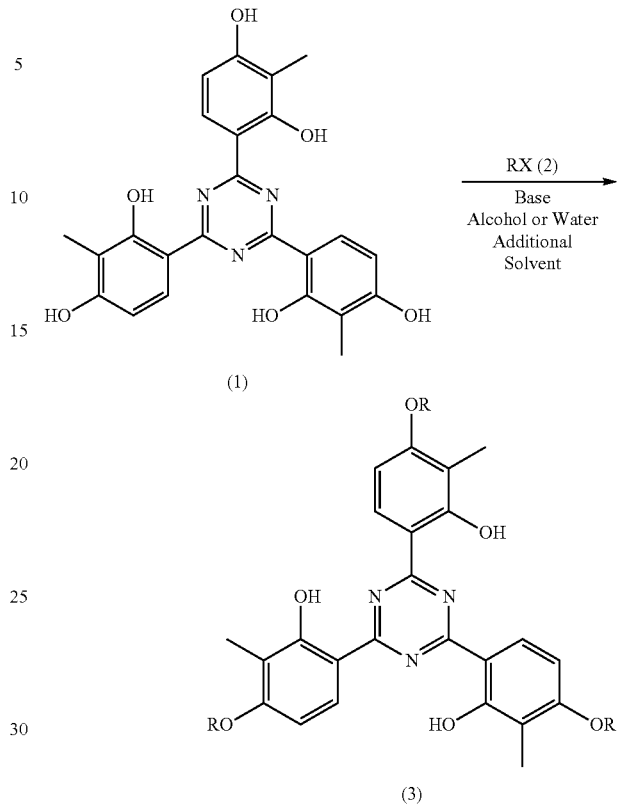

For example, an alcohol, or water is added to 2,4,6-tris (2,4-dihydroxy-3-methylphenyl)-1,3,5-triazine represented by the above formula (1). A base and, when necessary, an additional solvent are added and the temperature is adjusted, and thereafter, an alkylating agent is further added to carry out a reaction. When the 2,4,6-tris(2-hydroxy-3-methyl-4-alkoxyphenyl)-1,3,5-triazine compound is generated from the 2,4,6-tris(2,4-dihydroxy-3-methylphenyl)-1,3,5-triazine compound using an alcohol or water, there is an advantage that solubility decreases and precipitation occurs and thus the reaction does not proceed further.

The compound (1) used in the present process may be in a free form, or in a form of a salt with an acid such as hydrochloride, hydrobromide, sulfate and methanesulfonate, or an alkali metal salt such as a lithium salt, a sodium salt and potassium salt. Further, the compound (1) may be used in a form of a dry crystal, a wet crystal, or an extraction solution.

The alcohol is not particularly limited. However, examples of the alcohol include $C_{1-6}$ alkyl alcohols such as methanol, ethanol, n-propanol, isopropanol (2-propanol), n-butanol (1-butanol), t-butanol, pentyl alcohol, and hexyl alcohol (1-hexanol); $C_{3-6}$ cycloalkyl alcohols such as cyclopropanol, cyclobutanol, cyclopentanol, and cyclohexanol; polyvalent alcohols such as ethylene glycol; and the like. Preferred alcohols are methanol, ethanol, n-propanol, isopropanol, n-butanol, t-butanol, pentyl alcohol, and hexyl alcohol; more preferred alcohols are ethanol, n-propanol, isopropanol, n-butanol, t-butanol, and hexyl alcohol; even more preferred alcohols are ethanol, isopropanol, n-butanol, and t-butanol; and a particularly preferred alcohol is ethanol. These alcohols or water may each be independently used, or two or more of these alcohols or water may be used in combination.

Since water or alcohol is used in the present process, it is also possible to use an alcohol aqueous solution. A mixing ratio of water and alcohol in an alcohol aqueous solution may be appropriately adjusted. However, for example, a concentration of the alcohol can be set to about 5 wt % or more and about 95 wt % or less.

An amount of the alcohol or water to be used is not particularly limited. However, the amount of the alcohol or water with respect to 1 part by weight of the compound (1) is preferably 60 parts by weight or less, more preferably 30 parts by weight or less, and particularly preferably 15 parts by weight or less. A lower limit of the amount of the alcohol or water is not particularly limited, but is preferably 0.2 parts by weight or more, more preferably 0.5 parts by weight or more, and particularly preferably 1 part by weight or more.

Since the alcohol or water also serves as a reaction solvent, it is not particularly necessary to additionally add a solvent. However, an additional solvent may be further added for a purpose of improving a liquid property. Further, addition of an additional solvent may improve the yield and the like. The additional solvent is not particularly limited as long as the additional solvent does not affect the reaction. Specifically, for example, ether-based solvents such as tetrahydrofuran, methyl tetrahydrofuran, diethyl ether, 1,4-dioxane, methyl tert-butyl ether, and ethylene glycol dimethyl ether; nitrile-based solvents such as acetonitrile, and propionitrile; ester-based solvents such as ethyl acetate, n-propyl acetate, and isopropyl acetate; aliphatic hydrocarbon-based solvents such as pentane, hexane, heptane, and methylcyclohexane; aromatic hydrocarbon-based solvents such as benzene, toluene, xylene, ethylbenzene, and mesitylene; ketone-based solvents such as acetone, methyl ethyl ketone, and methyl isobutyl ketone; halogen-based solvents such as methylene chloride, and 1,2-dichloroethane; sulfoxide-based solvents such as dimethyl sulfoxide; amide-based solvents such as N,N-dimethylformamide, N,N-dimethylacetamide, N,N-diethylacetamide, N-methyl-2-pyrrolidone, N-ethyl-2-pyrrolidone, N-methyl-ε-caprolactam, and hexamethylphosphoramide; urea-based solvents such as dimethylpropylene urea; phosphonic acid triamide-based solvents such as hexamethylphosphonic acid triamide; and the like can be used. These additional solvents may each be independently used, or two or more of these additional solvents may be used in combination. When two or more of the additional solvents are used in combination, mixing ratios thereof are not particularly limited. Preferred additional solvents are amide-based solvents such as N,N-dimethylformamide, N,N-dimethylacetamide, N,N-diethylacetamide, N-methyl-2-pyrrolidone, N-ethyl-2-pyrrolidone, N-methyl-ε-caprolactam, and hexamethylphosphoramide. A more preferred additional solvent is N,N-dimethylformamide or N,N-dimethylacetamide.

An amount of the additional solvent to be used is not particularly limited and may be appropriately adjusted. However, for example, with respect to a total amount of the alcohol, water and the additional solvent, a proportion of the alcohol and water can be set to about 1 vol % or more and about 95 vol % or less. A proportion of the additional solvent is preferably 2 vol % or more, more preferably 5 vol % or more, and even more preferably 10 vol % or more, and is preferably 70 vol % or less or 60 vol % or less, more preferably 50 vol % or less or 30 vol % or less, and even more preferably 20 vol % or less.

The base is not particularly limited. However, preferred bases are an alkali metal hydroxide, an alkali metal alkoxide, an alkali metal carbonate, an alkali metal hydrogen carbonate, an alkaline earth metal hydroxide, an alkaline earth metal carbonate, an alkaline earth metal hydrogen carbonate; more preferred bases are a potassium hydroxide, a potassium alkoxide, a potassium carbonate, and a potassium hydrogen carbonate; and a particularly preferred base is a potassium carbonate. An amount of the base to be used is not particularly limited. However, the amount of the base with respect to 1 mole of the compound (1) is preferably 12 moles or less, more preferably 6 moles or less, and particularly preferably 3 moles or less. A lower limit of the amount of the base is not particularly limited, but is preferably 0.5 moles or more, more preferably 1 mole or more, and particularly preferably 2 moles or more.

An alkylating agent used in the present reaction is represented the above formula (2). An order of addition of the compound (1), the alcohol or water, the base, the additional solvent and the alkylating agent (2) in the present process is not particularly limited. However, the alkylating agent (2) is preferably added last. Here, R represents a $C_{1-10}$ alkyl group, and may any one of a $C_{1-10}$ straight chain alkyl group, a $C_{1-10}$ branched chain alkyl group, and a $C_{3-10}$ cycloalkyl group. Preferably, R is an ethyl group, an n-propyl group, an n-butyl group, an n-pentyl group, or an n-hexyl group, and is more preferably an n-butyl group or an n-hexyl group. Further, X represents a leaving group, and is preferably a halogen atom or a sulfonyloxy group, and is more preferably a bromine atom, an iodine atom, or a methanesulfonyloxy group. An amount of the alkylating agent (2) to be used is not particularly limited. However, the amount of the alkylating agent (2) with respect to 1 mole of the compound (1) is preferably 20 moles or less, more preferably 10 moles or less, and particularly preferably 5 moles or less. A lower limit of the amount of the alkylating agent (2) is not particularly limited, but is preferably 2 moles or more, more preferably 3 moles or more, and particularly preferably 4 moles or more.

A reaction temperature of the present process is not particularly limited, but is preferably not higher than a boiling point of the reaction solvent, more preferably 200° C. or lower, and particularly preferably 150° C. or lower. A lower limit of the reaction temperature is not particularly limited, but is preferably not lower than a melting point of the reaction solvent, more preferably 0° C. or higher, and particularly preferably 50° C. or higher.

After completion of the reaction, it is preferable to perform a general post-treatment. For example, the reaction solution is neutralized by adding an acid, and is cooled, and thereby a solid is precipitated. By filtering and washing the solid, the 2,4,6-tris(2-hydroxy-3-methyl-4-alkoxyphenyl)-1,3,5-triazine compound (3), which is a target product, is obtained.

The acid used for neutralization is not particularly limited. However, preferred acids are mineral acids such as hydrogen chloride, hydrogen bromide, sulfuric acid, and nitric acid; ammonium salts such as ammonium chloride, ammonium sulfate, and ammonium acetate; sulfonic acids such as trifluoromethanesulfonic acid, p-toluenesulfonic acid, and methanesulfonic acid. More preferred acids are hydrogen chloride, sulfuric acid, and ammonium chloride. A particularly preferred acid is ammonium chloride. These acids may each be directly used or may each be used as an aqueous solution.

An amount of the acid to be used is not particularly limited. However, the amount of the acid with respect to 1 mole of the compound (1) is preferably 20 moles or less, more preferably 10 moles or less, and particularly preferably 5 moles or less. A lower limit of the amount of the acid is not particularly limited, but is preferably 1 mole or more, more preferably 2 moles or more, and particularly preferably 4 moles or more. Further, a degree of the neutralization may be appropriately adjusted. However, for example, pH can be adjusted to 6.0 or more and 8.0 or less. In an excessive acidic state, there is a risk that the compound (1) may become a salt to increase its solubility and may be difficult to precipitate as a solid. On the other hand, in an excessive basic state, there is a risk that a salt corresponding to the base used may precipitate.

The temperature at which the solid is precipitated is not particularly limited, but is preferably 70° C. or lower, more preferably 50° C. or lower, and particularly preferably 30° C. or lower. A lower limit of the temperature at which the solid is precipitated is not particularly limited, but is preferably not lower than a melting point of the reaction solvent, more preferably −40° C. or higher, and particularly preferably −20° C. or higher.

A method for separating the solid is not particularly limited, but a solid of a target substance can be obtained using a method such as vacuum filtration, pressure filtration, or centrifugation.

The compound (3) as a target product has a purity sufficient to achieve its functions in this state. However, in a case where it is desired to further improve the purity, when necessary, recrystallization may be carried out. Here, a solvent used for recrystallization is preferably tetrahydrofuran, ethyl acetate, toluene, dimethylformamide, or water, and more preferably ethyl acetate.

Using the compound (3) produced using the method of the present invention, a polarizer protective film can be produced, and further, a polarizing plate can be produced. Specifically, at least the compound (3) produced using the method of the present invention and a thermoplastic resin are mixed to prepare a thermoplastic resin composition, and further, the thermoplastic resin composition is molded into a film-like shape, and thereby, a polarizer protective film can be produced. The polarizer protective film is a film that protects a polarizer from ultraviolet light and the like in a polarizing plate.

As the thermoplastic resin used in producing the polarizer protective film, a commonly known thermoplastic resin can be used. Examples of the thermoplastic resin include thermoplastic cellulose-based resins such as triacetyl cellulose; polyester-based resins such as polyethylene terephthalate; poly (meth)acrylic acid-based resins; and the like.

To prepare the thermoplastic resin composition, it is sufficient that the thermoplastic resin composition to be used is heated to at least a melting temperature thereof and is melt-kneaded with at least the compound (3). In thermoplastic resin composition, other materials such as a filler, an antioxidant, a heat deterioration inhibitor, a light stabilizer, a lubricant, a release agent, a polymer processing aid, an antistatic agent, a flame retardant, a dye pigment, a light diffusing agent, an organic dye, a delustering agent, an impact modifier, a foaming agent, a filler, and a fluorescence substance may be added.

The thermoplastic resin composition may be formed into a polarizer protective film by being molded into a film-like shape using, for example, a solution casting method, a melt extrusion method, a calendar method, a compression molding method, or the like. Further, uniaxial extension or biaxial extension may also be performed. a thickness of the film may be appropriately adjusted. However, for example, the thickness of the film can be about 10 μm or more and about 300 μm or less.

A polarizing plate can be produced by laminating the polarizer protective film on at least one side of a polarizer. As the polarizer, a general polarizer can be used. For example, a film obtained by adsorbing a dichroic substance such as iodine or a dichroic dye on a hydrophilic film such as a polyvinyl alcohol-based film and unixially stretching the hydrophilic film can be used. A thickness of the polarizer is not particularly limited. However, for example, the thickness of the polarizer can be about 1 μm or more and 100 μm or less. The polarizer protective film can be laminated on the polarizer using an ordinary lamination method.

The present application claims benefit of priority based on Japanese Patent Application No. 2015-177994 filed on Sep. 9, 2015. The entire content of the specification of Japanese Patent Application No. 2015-177994 filed on Sep. 9, 2015 is incorporated herein by way of reference.

EXAMPLES

In the following, embodiments of the production method of the 2,4,6-tris(2-hydroxy-3-methyl-4-alkoxyphenyl)-1,3,5-triazine compound and the production method of the 2,4,6-tris(2,4-dihydroxy-3-methylphenyl)-1,3,5-triazine are described. However, the present invention is not limited to these.

In the present Example, yield and quality of a compound were analyzed using high-performance liquid chromatography. Further, purity (area %) refers to an area of an object with respect to a total peak area after subtracting a solvent peak and a peak shape (hereinafter referred to as "blank") caused by a system-derived waveform disturbance. Further, each impurity amount (area %) refers to an area of each impurity with respect to an area of an object.

<High-Performance Liquid Chromatography Analysis Conditions in Triarylation Process>
Column: Senshu Pal PEGASIL ODS
   4.6 mmI.D.×250 mm
Column temperature: 40° C.
Flow rate: 0.8 mL/min
Detection wavelength: 345 nm
Mobile phase A: distilled water
Mobile phase B: tetrahydrofuran
Injection volume: 10 μL
Gradient Pattern
0.00 minutes Mobile phase A:Mobile phase B=50:50
5.00 minutes Mobile phase A:Mobile phase B=50:50
25.00 minutes Mobile phase A:Mobile phase B=25:75
30.00 minutes Mobile phase A:Mobile phase B=25:75
30.01 minutes Mobile phase A:Mobile phase B=50:50
40.00 minutes STOP
<High-Performance Liquid Chromatography Analysis Conditions in Trialkylation Process>
Column: Senshu Pal PEGASIL ODS
   4.6 mmI.D.×250 mm
Column temperature: 40° C.
Flow rate: 0.8 mL/min
Detection wavelength: 345 nm
Mobile phase A: distilled water
Mobile phase B: tetrahydrofuran
Injection volume: 10 μL
Gradient Pattern
0.00 minutes Mobile phase A:Mobile phase B=35:65
30.00 minutes Mobile phase A:Mobile phase B=25:75
35.00 minutes Mobile phase A:Mobile phase B=20:80
45.00 minutes Mobile phase A:Mobile phase B=20:80
45.01 minutes Mobile phase A:Mobile phase B=35:65
55.00 minutes STOP <Reaction Conversion Rate of 2,4,6-Tris(2,4-Dihydroxy-3-Methylphenyl)-1,3,5-Triazine>

The following reaction conversion rate and purity were calculated from the following formulas based on peak areas of a high-performance liquid chromatography chart. Further, in the calculation of the reaction conversion rate, impurities other than a di-substituted [2-chloro-4,6-di(2,4-dihydroxy-3-methylphenyl)-1,3,5-triazine] are not taken into consideration in the calculation formula since a production amount thereof is extremely small.

{[peak area of 2,4,6-tris(2,4-dihydroxy-3-methylphenyl)-1,3,5-triazine]/[peak area of 2-chloro-4,6-di(2,4-dihydroxy-3-methylphenyl)-1,3,5-triazine+ peak area of 2,4,6-tris(2,4-dihydroxy-3-methylphenyl)-1,3,5-triazine]}×100

<Reaction Conversion Rate of 2,4,6-Tris(2-Hydroxy-3-Methyl-4-Hexyloxyphenyl)-1,3,5-Triazine>

Similarly, impurities other than di-substituted [2-(2,4-dihydroxy-3-methylphenyl)-4,6-di(2-hydroxy-3-methyl-4-hexyloxyphenyl)-1,3,5-triazine] are not taken into consideration in the calculation formula since a production amount thereof is extremely small.

{Peak area of [2,4,6-tris(2-hydroxy-3-methyl-4-hexyloxyphenyl)-1,3,5-triazine]/[peak area of [2-(2,4-dihydroxy-3-methylphenyl)-4,6-di(2-hydroxy-3-methyl-4-hexyloxyphenyl)-1,3,5-triazine+peak area of 2,4,6-tris(2-hydroxy-3-methyl-4-hexyloxyphenyl)-1,3,5-triazine]}×100

<Purity>

Purity of a target substance was calculated from a HPLC chart using the following calculation formula.

{(Peak area of target substance)/[(total peak area)−(peak area of blank measurement)}×100

Example 1

Triarylation Process

Cyanuric chloride (20.00 g, 108.5 mmol), chlorobenzene (369.60 g, 18.48 wt/wt), and ethyl acetate (180.00 g, 9.00 wt/wt) were added and the temperature was adjusted to 40° C. Aluminum chloride (21.70 g, 1.50 equivalents) was added over 10 minutes using a solid inlet tube, and thereafter, 2-methylresorcinol (47.14 g, 3.50 equivalents) was added over 30 minutes. Here, "wt/wt" means a weight ratio with respect to cyanuric chloride. After allowing a reaction to proceed at 40° C. for 25 hours, a reaction conversion rate was 97%. Toluene (217.40 g, 10.87 wt/wt) was added, and thereafter, the temperature was raised to 80° C. 18 wt % hydrochloric acid (85.90 g, 3.80 equivalents) was added and the temperature was raised to 86° C., and decomposition of aluminum chloride was carried out over 1 hour, and thereafter, dehydration by heating distillation was carried out for 4 hours. After cooling to 25° C., filtration was carried out with a Buchner funnel to obtain a crude product of the compound (1). The obtained crude product was reslurried with water (660.00 g, 33.00 wt/wt), and thereafter, filtration was carried out with a Buchner funnel to obtain the compound (1) (yield 93%, purity 96.9 area %, the compound (4) was not detected).

Examples 2-15

Triarylation Process

The operation of the above Example 1 was followed except that additives, reaction temperatures and reagent amounts were set as shown in Table 1. The results are shown in Table 1. The compound (4) was not detected in all of Examples 2-15.

TABLE 1

| | | Reaction temperature (° C.) | Reagent amounts | | | Reaction conversion rate (%) | Yield (%) | Purity (area %) |
| --- | --- | --- | --- | --- | --- | --- | --- | --- |
| | Additive | | Additive (wt/wt) | Toluene (wt/wt) | HCl (equivalent) | | | |
| Example 2 | Isopropyl acetate | 40 | 1 | 11 | 4 | 91 | — | 89.7 |
| Example 3 | | 40 | 4 | — | — | 91 | — | 89.8 |
| Example 4 | | 40 | 8 | — | — | 91 | — | 90.0 |
| Example 5 | | 25 | 1 | — | — | 91 | — | 90.0 |
| Example 6 | | 60 | 4 | — | — | 92 | — | 91.2 |
| Example 7 | | 40 | 1 | 11 | 4 | 95 | 90 | 97.1 |
| Example 8 | | 40 | 8 | 33 | 4 | 93 | 89 | 94.2 |
| Example 9 | | 40 | 4 | 11 | 4 | 92 | 88 | 93.9 |
| Example 10 | | 40 | 6 | 11 | 4 | 94 | 91 | 94.9 |
| Example 11 | Hexyl acetate | 40 | 6 | 11 | 4 | 95 | 93 | 95.6 |
| Example 12 | Ethyl acetate | 40 | 6 | 11 | 4 | 98 | 96 | 97.8 |
| Example 13 | | 40 | 9 | — | — | 97 | — | 97.7 |
| Example 14 | | 40 | 9 | 11 | 4 | 98 | 94 | 90.5 |
| Example 15 | | 40 | 12 | — | — | 96 | — | 96.9 |

Comparative Example 1

Use of CPME in Triarylation Process

Cyanuric chloride (2.50 g, 13.6 mmol), 2-methylresorcinol (5.91 g, 3.50 equivalents), aluminum chloride (2.72 g, 1.50 equivalents), chlorobenzene (46.20 g, 18.48 wt/wt), and cyclopentyl methyl ether (2.45 g, 0.98 wt/wt, CPME) were added and the mixture was allowed to react at 80° C. for 2 hours. At 80° C., 18 wt % hydrochloric acid (10.76 g, 3.8 equivalents) was added and the temperature was raised to 90° C., and decomposition of aluminum chloride was carried out over 1 hour, and thereafter, toluene (27.18 g, 10.87 wt/wt) was added and reflux dehydration was carried out for 2 hours. After cooling to 25° C., filtration was carried out with a Buchner funnel to obtain the compound (1) (3.88 g, yield: 64%, purity: 80.9 area %, containing 14.7 area % of the compound (4)). In this way, when cyclopentyl methyl ether was used as an additive, the compound (4) as an impurity was generated, and the yield and purity of the target compound decreased.

Comparative Example 2

Use of CPME in Triarylation Process

Cyanuric chloride (15.00 g, 81.34 mmol), chlorobenzene (277.2 g, 18.48 wt/wt), cyclopentyl methyl ether (14.70 g, 0.98 wt/wt) were added and the temperature was adjusted to 25° C. Aluminum chloride (16.27 g, 1.50 equivalents) was added over 1 hour using a solid inlet tube, and thereafter, 2-methylresorcinol (35.34 g, 3.50 equivalents) was added over 1 hour. After allowing the mixture to react at 25° C. for 18 hours, a reaction intermediate represented by the following formula (6):

[Chemical Formula 8]

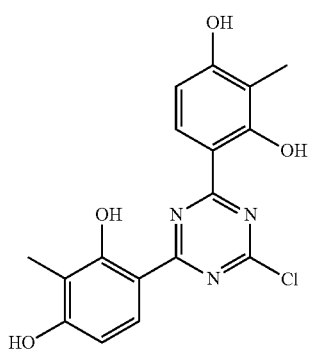

(6)

remained, and the reaction conversion rate was 93%. Subsequently, the same post-treatment as in Comparative Example 1 was carried out to obtain the compound (1) (30.28 g, yield: 83%, purity: 88.6 area %, containing 4.3 area % of the compound (4)).

Comparative Example 3

Examination of Additives in Triarylation Process

Cyanuric chloride (0.50 g, 2.7 mmol), chlorobenzene (9.24 g, 18.48 wt/wt), dibutyl ether (0.49 g, 0.98 wt/wt) were added and the temperature was adjusted to 25° C. After adding aluminum chloride (0.54 g, 1.5 equivalents), 2-methylresorcinol (1.18 g, 3.50 equivalents) was added, and the mixture was allowed to react at 25° C., and stirring became difficult due to deterioration of a liquid property. The reaction conversion rate was 62%.

Comparative Examples 4-15

Examination of Additives in Triarylation Process

The operation of the above Comparative Example 3 was followed except that additives were changed. In a case where an ether-based solvent, a nitrile-based solvent, an amide-based solvent, a ketone-based solvent, or a sulfoxide-based solvent was used as an additive, or in a case where no additive was used, deterioration of a liquid property, poor reaction, or a low reaction conversion rate was a problem.

Examples 16-18

Examination of Additives in Triarylation Process

In a case where an ester-based solvent was used as an additive, the liquid property was good and the reaction conversion rate was also equal to or higher than that of Comparative Example 2.

The results of Comparative Examples 2-15 and Examples 16-18 are shown in Table 2. In Table 2, regarding the liquid property, a case where the viscosity of the reaction solution excessively increased and stirring became difficult was regarded as "bad" and a case where the viscosity of the reaction solution did not excessively increase and stirring could be continued was regarded as "good."

TABLE 2

| | Additive | Classification | Reaction conversion rate (%) | Liquid property |
|---|---|---|---|---|
| Comparative Example 2 | Cyclopentyl methyl ether | Ether | 93 | Good |
| Comparative Example 3 | Dibutyl ether | | 62 | Bad |
| Comparative Example 4 | 4-Methyltetrahydropyran | | 39 | Bad |
| Comparative Example 5 | 2-Methyltetrahydrofuran | | 24 | Bad |
| Comparative Example 6 | Dioxane | | 92 | Bad |
| Comparative Example 7 | Chloroanisole | | 79 | Bad |
| Comparative Example 8 | Methyl t-butyl ether | | Reaction did not proceed | Bad |
| Comparative Example 9 | Tetrahydrofuran | | Reaction did not proceed | Good |
| Comparative Example 10 | 1,3-Dioxane | | Reaction did not proceed | Good |
| Comparative Example 11 | Acetonitrile | Nitrile | 56 | Good |
| Comparative Example 12 | Dimethylacetamide | Amide | Reaction did not proceed | Bad |
| Comparative Example 13 | Methyl isobutyl ketone | Ketone | 69 | Good |
| Comparative Example 14 | Dimethylsulfoxide | Sulfoxide | Reaction did not proceed | Bad |
| Comparative Example 15 | | None | 94 | Bad |
| Example 16 | Ethyl acetate | Ester | 98 | Good |
| Example 17 | Isopropyl acetate | | 94 | Good |
| Example 18 | Hexyl acetate | | 95 | Good |

Example 19

Reaction Using Alcohol and Water as Reaction Solvent in Trialkylation Process The compound (1) (25.87 g, 57.82 mmol), and ethanol (170.74 g, 6.60 wt/wt) were added and the temperature was adjusted to 22° C. Potassium carbonate (19.18 g, 2.40 equivalents) and hexyl bromide (42.00 g, 4.40 equivalents) were added and the temperature was adjusted to 76° C., and the mixture was allowed to react under reflux for 40 hours. After neutralization by adding water (170.74 g, 6.6 wt/wt) and ammonium chloride (14.85 g, 4.80 equivalents) and cooling to 25° C., a solid precipitated. By filtering and washing the solid, a crude product of the compound (3) was obtained. Ethyl acetate (150.00 g, 5.00 wt/wt) was added to the crude product to dissolve the crude product at 57° C., and thereafter, the mixture was cooled to 1° C., and was aged for 15 hours. By subjecting this to filtration and washing, the compound (3) (32.74 g, 81%, purity: 99.0 area %, both a later-described compound (7) and a later-described compound (8) were not detected) was obtained. A yield of the compound (5) was 2% and a whole amount thereof was removed to a crystallization mother liquor.

[Chemical Formula 9]

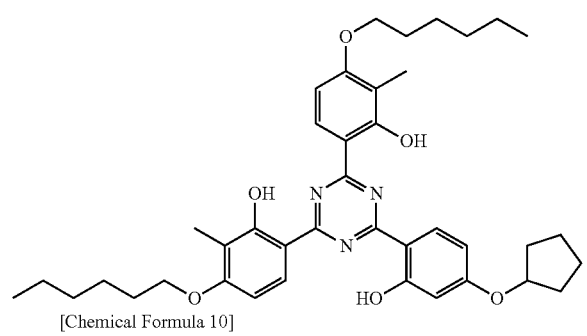

(7)

[Chemical Formula 10]

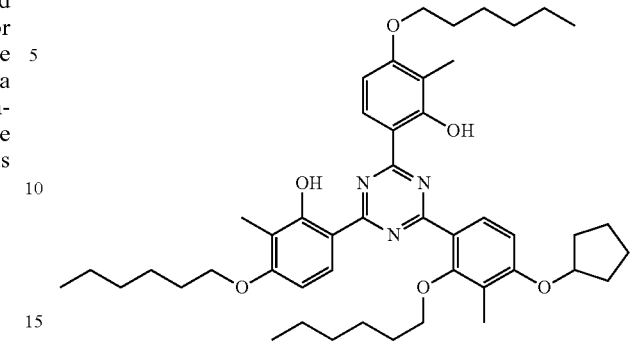

(8)

Examples 20-29

Trialkylation Process

The operation of the above Example 19 was followed except that reaction solvents, alkylating agents, reaction temperatures and reaction solvent amounts were set as shown in Table 3. The results are shown in Table 3. In Table 3, "DMA" means N,N-dimethylacetamide.

TABLE 3

| | Reaction solvent | Alkylating agent | Reaction temperature (° C.) | Reaction solvent amount (wt/wt) | Compound (5) Yield (%) | Compound (3) Yield (%) | Compound (3) purity (area %) |
|---|---|---|---|---|---|---|---|
| Example 20 | Isopropanol | Hexyl bromide | 79 | 7 | 2 | 85 | 96.8 |
| Example 21 | | | 79 | 10 | 3 | 88 | 94.2 |
| Example 22 | | | 79 | 10 | 3 | 89 | 94.7 |
| Example 23 | | Butyl bromide | 79 | 7 | 2 | 96 | 89.4 |
| Example 24 | | Hexyl methanesulfonate | 79 | 7 | 5 | 84 | 86.9 |
| Example 25 | | Hexyl bromide iodide | 79 | 7 | 3 | 77 | 86.6 |
| Example 26 | n-Butanol | Hexyl iodide | 108 | 7 | 1 | 81 | 98.7 |
| Example 27 | Hexyl alcohol | | 135 | 7 | 4 | 79 | 98.0 |
| Example 28 | n-propanol | | 97 | 7 | 1 | 83 | 92.9 |
| Example 29 | H$_2$O/DMA | | 100 | 1 (H$_2$O) 5 (DMA) | 5 | 83 | 86.9 |

As shown in Table 3, when water or alcohol was used as a solvent, both the yield and the purity of the target compound (3) were good.

Comparative Example 16

Examination of Solvents in Trialkylation Process

The compound (1) (1.00 g, 2.23 mmol), potassium carbonate (0.556 g, 1.80 equivalents), and N,N-dimethylformamide (5.27 g, 5.27 wt/wt) were added and the temperature was adjusted to 90° C. Hexyl bromide (1.22 g, 3.30 equivalents) was added thereto, and the mixture was allowed to react at 90° C. for 2 hours. After cooling the reaction solution to 25° C., chloroform (16.54 g, 16.54 wt/wt) and water (5.59 g, 5.59 wt/wt) were added and a product was extracted into an organic layer. The organic layer was dried with anhydrous sodium sulfate, and thereafter, the solvent was distilled off to obtain a solid phase. By recrystallizing the solid phase from ethyl acetate, the compound (3) (1.00 g, yield: 64%, purity: 94.8 area %, containing 1.06 area % of the compound (7) and 3.93 area % of the compound (8)) was obtained. In this way, in the case where only N,N-dimethylformamide was used as a reaction solvent, the yield was reduced, and impurities were generated and mixed with the target compound (3).

Comparative Example 17

Examination of Solvents in Trialkylation Process

The compound (1) (2.00 g, 4.47 mmol), potassium carbonate (1.48 g, 2.4 equivalents) and N,N-dimethylformamide (10.54 g, 5.27 wt/wt) were added and the temperature was adjusted to 60° C. Hexyl bromide (3.25 g, 4.4 equivalents) was added thereto, and the mixture was allowed to react at 60° C. for 23 hours. Ethyl acetate (33.08 g, 16.54 wt/wt) and water (15.52 g, 7.76 wt/wt) were added and the mixture was cooled to 75° C., and thereafter, a product was extracted to an organic layer, and the organic layer was further washed with water (4.00 g, 2 wt/wt). A solvent of the organic layer was distilled off to obtain a solid phase. Ethyl acetate (28.92 g, 14.46 wt/wt) was added to the solid phase to dissolve the solid phase at 75° C., and thereafter, the mixture was cooled to 0° C. and was aged for 1 hour. By subjecting this to separation and drying, the compound (3) (2.10 g, 67%, yield, purity: 98.9 area %, both the compound (7) and the compound (8) were not detected) was obtained. The yield of the compound (5) was 14% and a whole amount thereof was removed to a crystallization mother liquor. In this way, in the case where only N,N-dimethylformamide was used as a reaction solvent, the yield was reduced, and impurities were generated and mixed with the target compound (3).

What is claimed is:

1. A method of producing a 2,4,6-tris(2-hydroxy-3-methyl-4-alkoxyphenyl)-1,3,5-triazine compound of formula (3), comprising:
    performing a reaction, in a solvent comprising ethanol, in presence of a base, between 2,4,6-tris(2,4-dihydroxy-3-methylphenyl)-1,3,5-triazine of formula (1) and an alkylating agent of formula (2), wherein the formula (1) is

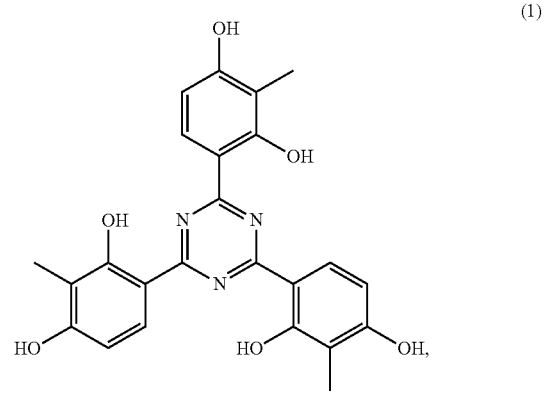

the formula (2) is RX, where R represents a $C_{1-10}$ alkyl group, and X represents a leaving group, and
the formula (3) is

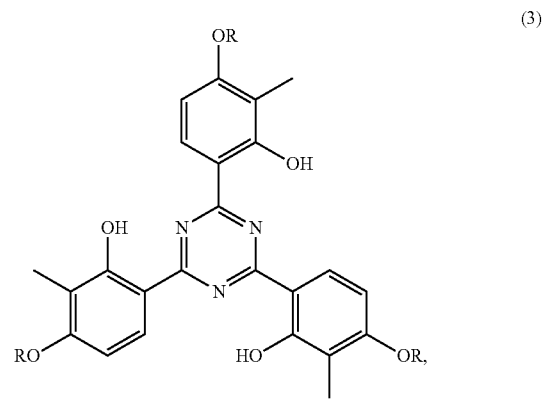

where R in the formula (3) represents a $C_{1-10}$ alkyl group.

2. The method of claim 1, wherein R in the formulas (2) and (3) is a hexyl group or a butyl group.

3. The method of claim 1, wherein X is a bromine atom, an iodine atom, or a methanesulfonyloxy group.

4. The method of claim 1, further comprising:
    adding an acid aqueous solution after the reaction such that a reaction solution is neutralized and the compound of the formula (3) is obtained as a solid.

5. The method of claim 1, further comprising:
    performing a reaction between cyanuric chloride and 2-methylresorcinol in presence of a Lewis acid and an ester compound such that the compound of the formula (1) is produced.

6. The method of claim 5, wherein the ester compound is at least one selected from the group consisting of ethyl acetate, isopropyl acetate, and hexyl acetate.

7. A method of producing 2,4,6-tris(2,4-dihydroxy-3-methylphenyl)-1,3,5-triazine of formula (1):

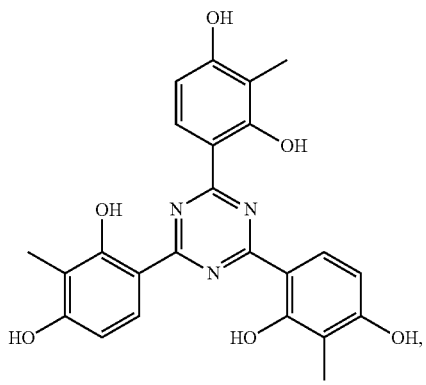

comprising:
performing a reaction between cyanuric chloride and 2-methylresorcinol in presence of a Lewis acid and at least one selected from the group consisting of ethyl acetate, isopropyl acetate, and hexyl acetate.

8. A method of producing a polarizer protective film, comprising:
performing a reaction, in a solvent comprising ethanol, in presence of a base, between 2,4,6-tris(2,4-dihydroxy-3-methylphenyl)-1,3,5-triazine of formula (1) and an alkylating agent of formula (2), such that a 2,4,6-tris(2-hydroxy-3-methyl-4-alkoxyphenyl)-1,3,5-triazine compound of formula (3) is produced;
mixing at least a thermoplastic resin and the compound of the formula (3) such that a thermoplastic resin composition is obtained; and
forming the thermoplastic resin composition into a film-like shape,
wherein the formula (1) is

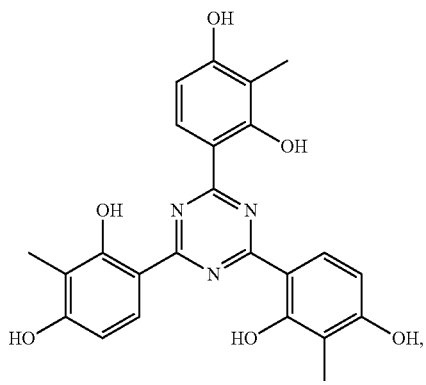

the formula (2) is RX, where R represents a $C_{1-10}$ alkyl group, and X represents a leaving group, and
the formula (3) is

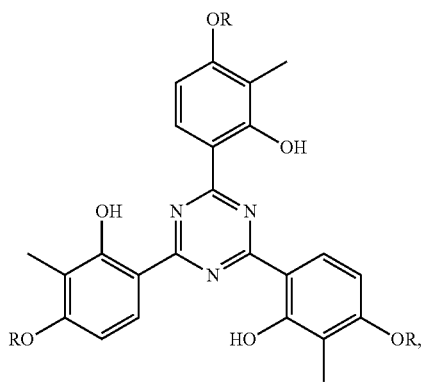

where R in the formula (3) represents a $C_{1-10}$ alkyl group.

9. A method of producing a polarizing plate, comprising:
producing a polarizer protective film by the method of claim 8; and
laminating the produced polarizer protective film on at least one side of a polarizer.

10. The method of claim 2, wherein X is a bromine atom, an iodine atom, or a methanesulfonyloxy group.

11. The method of claim 1, wherein the solvent is ethanol.

12. The method of claim 2, wherein the solvent is ethanol.

13. The method of claim 3, wherein the solvent is ethanol.

14. The method of claim 2, further comprising:
adding an acid aqueous solution after the reaction such that a reaction solution is neutralized and the compound of the formula (3) is obtained as a solid.

15. The method of claim 3, further comprising:
adding an acid aqueous solution after the reaction such that a reaction solution is neutralized and the compound of the formula (3) is obtained as a solid.

16. The method of claim 1, wherein the solvent comprises isopropanol, and R in the formulas (2) and (3) is a hexyl group.

* * * * *